(12) United States Patent
Maselli (10) Patent No.: US 9,724,485 B2
(45) Date of Patent: Aug. 8, 2017

(54) DEVICE FOR RESUSCITATING VICTIMS OF CARDIO-RESPIRATORY ARREST (71) Applicant: Javier Ernesto Maselli, Barcelona (ES)

(72) Inventor: Javier Ernesto Maselli, Barcelona (ES)

( * ) Notice: Subject to any disclaimer, the term of this patent is extended or adjusted under 35 U.S.C. 154(b) by 376 days.

(21) Appl. No.: 14/354,432

(22) PCT Filed: Sep. 25, 2012

(86) PCT No.: PCT/ES2012/070665
§ 371 (c)(1),
(2) Date: Apr. 25, 2014

(87) PCT Pub. No.: WO2013/060911
PCT Pub. Date: May 2, 2013

(65) Prior Publication Data
US 2014/0299127 A1    Oct. 9, 2014

(30) Foreign Application Priority Data

Oct. 26, 2011    (ES) .................................. 201101183

(51) Int. Cl.
*A61M 16/00*    (2006.01)
*A61M 16/20*    (2006.01)
(Continued)

(52) U.S. Cl.
CPC .... *A61M 16/0048* (2013.01); *A61M 16/0493* (2014.02); *A61M 16/1055* (2013.01);
(Continued)

(58) Field of Classification Search
CPC .......... A61M 16/0048; A61M 16/0493; A61M 16/208; A61M 16/06; A61M 16/0084;
(Continued)

(56) References Cited

U.S. PATENT DOCUMENTS 3,099,985 A     8/1963  Wilson et al.
3,124,124 A  *  3/1964  Cross ................ A61M 16/0048
                                                128/203.11
(Continued)

FOREIGN PATENT DOCUMENTS

CN      201543069 U    8/2010
DE      20000369 U1    6/2001
(Continued)

*Primary Examiner* — Peter S Vasat
*Assistant Examiner* — Margaret Luarca
(74) *Attorney, Agent, or Firm* — Hayes Soloway PC (57) ABSTRACT The present invention comprises an insufflated air inlet (2*a*), an outlet (3*a*) for said insufflated air provided at the lower end of an air conveying tube (3) designed to penetrate the throat of the victim through the mouth, at least a first one-way valve (4) interposed between said air inlet (2*a*) and air outlet (3*a*) to allow the flow of air from said inlet (2*a*) to said outlet (3*a*) and prevent the flow of a fluid exhaled by the victim in the opposite direction, the body of said valve (4) including an outlet aperture (4*a*) for the exit of the fluid exhaled by the victim, and characterized in that the upper end of said insufflated air conveying tube (3) comprises a portion (3*b*) of tube (3) which is configured for internally receiving the body of said valve (4), the wall of said tube (3) including at least one outer hole (6) communicating with the aperture (4*a*) of the body of the valve (4) to allow discharging the fluid exhaled by the victim to the outside.

12 Claims, 8 Drawing Sheets (51) Int. Cl.
*A61M 16/10* (2006.01)
*A61M 16/06* (2006.01)
*A61M 16/04* (2006.01)

(52) U.S. Cl.
CPC ....... *A61M 16/208* (2013.01); *A61M 16/0084* (2014.02); *A61M 16/0495* (2014.02); *A61M 16/06* (2013.01); *A61M 2205/0205* (2013.01); *A61M 2205/7509* (2013.01); *A61M 2205/7518* (2013.01)

(58) Field of Classification Search
CPC .......... A61M 16/0495; A61M 16/0465; A61M 16/0463; A61M 16/0488; A61M 16/0409; A61M 2205/0205
USPC ........................... 128/202.28, 202.29, 203.11
See application file for complete search history.

(56) References Cited

U.S. PATENT DOCUMENTS

| | | | | |
|---|---|---|---|---|
| 3,352,304 A * | 11/1967 | Bartlett, Jr. | ........... | A61M 16/00 128/202.29 |
| 3,356,100 A | 12/1967 | Seeler | | |
| 4,579,114 A | 4/1986 | Gray et al. | | |
| 5,398,674 A * | 3/1995 | Martin | ............. | A61M 16/0048 128/202.28 |
| 5,584,288 A * | 12/1996 | Baldwin | ........... | A61M 16/0048 128/202.28 |
| 5,735,265 A * | 4/1998 | Flynn | ................ | A61M 16/0048 128/202.28 |
| 7,066,174 B1 | 6/2006 | Smith et al. | | |
| 8,251,066 B1 * | 8/2012 | Ho | ........................ | A61M 16/06 128/204.18 |
| 2004/0194785 A1 | 10/2004 | Miller | | |
| 2005/0139220 A1 * | 6/2005 | Christopher | .......... | A61M 16/04 128/207.14 |
| 2007/0125373 A1 | 6/2007 | Westfall | | |
| 2009/0056721 A1 * | 3/2009 | Leboeuf | ............ | A61M 16/0488 128/207.14 |
| 2010/0101573 A1 | 4/2010 | Foley et al. | | |

FOREIGN PATENT DOCUMENTS

| | | | | |
|---|---|---|---|---|
| FR | 1600919 | 8/1970 | | |
| FR | WO 9808436 A1 * | 3/1998 | ............ | A61B 5/097 |
| GB | 901357 A | 7/1962 | | |
| GB | 2176406 | 12/1986 | | |
| GB | 2303556 A | 2/1997 | | |

* cited by examiner

DEVICE FOR RESUSCITATING VICTIMS OF CARDIO-RESPIRATORY ARREST

The present invention relates to a device for resuscitating victims of cardiorespiratory arrest. Particularly, the present invention relates to an oropharyngeal resuscitation device which is inserted into the mouth of the victim to perform a cardiopulmonary resuscitation procedure while the resuscitator carries out cardiac massages.

BACKGROUND OF THE INVENTION

Cardiopulmonary resuscitation (CPR) or cardiorespiratory resuscitation (CRR) is a series of internationally standardized emergency procedures intended for assuring oxygen supply to vital organs when blood circulation of an individual stops suddenly, regardless of the cause of the cardiorespiratory arrest.

Intubation by means of a tube which serves to connect an artificial respirator to the airways of the victim or patient is considered the most optimal procedure to assure artificial ventilation. However, there is substantial evidence indicating that without suitable or continuous training for maintaining skills, the incidence of complications is very high.

The use of tubes or cannulas for insufflating air manually to the airways of the victim of cardiorespiratory arrest is known. Some of these tubes or cannulas have one-way valves that prevent the flow of fluids exhaled by the victim in the opposite direction for the purpose of protecting the resuscitator.

U.S. Pat. No. 4,579,114 describes a resuscitation device of the mentioned type which has an air conveying tube configured for penetrating the throat of the victim and a one-way valve interposed between an air inlet nozzle for the entry of air coming from the resuscitator and the air outlet of said conveying tube. The same device includes an additional flexible air conveying tube which is attached to the valve at one end and to the air inlet nozzle for the resuscitator at the other end.

The device of U.S. Pat. No. 4,579,114 has the advantage that the additional flexible tube which is attached to the nozzle makes the resuscitation procedure easier since the resuscitator can orient the flexible tube in the position he/she deems most comfortable. However, it has been observed that this additional flexible tube reduces effective air entry of the device and complicates handling.

DESCRIPTION OF THE INVENTION

The objective of the present invention is to solve the drawbacks of the devices of the state of the art by means of developing a device for resuscitation having the advantages that will be described below.

According to this objective, the present invention provides a device for resuscitating victims of cardiorespiratory arrest comprising an insufflated air inlet, an outlet for said insufflated air provided at the lower end of an air conveying tube designed to penetrate the throat of the victim through the mouth, and at least a first one-way valve interposed between said air inlet and air outlet to allow the flow of air from said inlet to said outlet and prevent the flow of a fluid exhaled by the victim in the opposite direction, the body of said valve including an outlet aperture for the exit of the fluid exhaled by the victim.

The device is characterized in that the upper end of said insufflated air conveying tube comprises a portion of tube which is configured for internally receiving the body of said valve, the wall of said tube including at least one outer hole communicating with the aperture of the body of the valve to allow discharging the fluid exhaled by the victim to the outside.

The claimed device has the advantage that the body of the valve is housed inside the air conveying tube which penetrates the throat of the victim, so the air can be insufflated directly from said tube without needing an additional tube. As a result, a device having a very compact design that improves effective air entry is obtained.

Furthermore, the claimed device is safer than the devices of the state of the art because the walls of the conveying tube protect the body of the valve since the valve is housed inside this tube. The entry of dust or dirt which can result in the device malfunctioning is therefore prevented.

Another advantage of the device lies in the fact that, as a result of its compact design, it can be assembled and disassembled in a very convenient manner without needing adhesives. Furthermore, it is an easy-to-handle device that can be held by the air conveying tube which penetrates the throat without the risk of damaging the valve.

Said insufflated air inlet is preferably provided with a nozzle for contact with the mouth of the resuscitator, including coupling means for coupling to the upper end of said air conveying tube.

As a result, the resuscitator can comfortably insufflate air directly from the upper end of the air conveying tube which penetrates the throat of the victim in a completely effective manner and without needing any additional tube.

Said nozzle advantageously comprises a seat provided with a layer of foam for retaining moisture and/or microbes present in the insufflated air.

The coupling means of the nozzle are preferably configured to allow the rotation of said nozzle in both directions about the axis of said air conveying tube.

The resuscitator can therefore change the position of the nozzle to orient it in the best possible way depending on the position of the victim.

Furthermore, the body of said valve and said nozzle are advantageously integrated in a single part, said part being able to be coupled to and uncoupled from the upper end of said air conveying tube.

As a result, the nozzle and valve assembly can be comfortably removed for cleaning.

According to a preferred embodiment, the lower end of said air conveying tube comprises a curved portion of the tube designed to penetrate the pharynx of the victim, said curved portion of the tube allowing holding down the tongue of the victim to prevent choking and self-inflicted biting injuries.

The outer wall of said air conveying tube advantageously comprises a ring abutting against the teeth and/or gums of the victim and said air conveying tube is preferably made of a soft translucent plastic material to be able to see if the victim bleeds or vomits.

Furthermore, the outer hole of the air conveying tube allowing the exit of the fluid exhaled by the victim is advantageously arranged at a height greater than the height of the aperture of the first valve.

The aperture of the valve is therefore protected by the walls of the tube itself.

According to the same preferred embodiment, said device comprises a second one-way safety valve which is interposed between said first one-way valve and said nozzle, said second one-way valve preventing the flow of a fluid exhaled by the victim in the opposite direction in the event that the first valve malfunctions.

Said second one-way valve preferably comprises a membrane for closing the passage of fluid towards the nozzle, said membrane being able to be bent by the insufflated air pressure for opening the passage of air towards the first one-way valve.

According to the same preferred embodiment, said first one-way valve comprises an obturating piston which is associated with a spring, said obturating piston being able to move inside the body of said valve to allow the entry of air when the insufflated air pressure exceeds the reaction force of the spring, the body of the valve comprising guides along which said piston moves, said piston closing the outlet aperture of the body of the valve as it moves along said guides due to the insufflated air pressure.

This valve of the piston has the advantage that it effectively prevents the flow of fluid exhaled by the victim in the opposite direction, the guides of the body of the valve assuring the correct movement of said piston.

The body of said first valve advantageously comprises a pair of holes for inserting the ends of said spring, the wall of the air conveying tube abutting against said ends when the body of the first valve is housed therein.

Said device preferably comprises a protective mask acting as a barrier for the lips, nose and part of the face of the resuscitator which is configured for being coupled to the air inlet nozzle of the device, said mask being able to rotate together with said nozzle about the axis of the air conveying tube.

Furthermore, said device preferably comprises a second mask for covering the mouth and nose of the victim, said second mask being configured to be coupled to the upper end of said air conveying tube.

Optionally, said device comprises an accessory for connecting the nozzle to a self-expandable resuscitation bag or balloon for insufflating air.

In the present invention, fluid exhaled by the victim will be understood as any type of fluid, either exhaled air or body fluids, such as blood or vomit, for example.

BRIEF DESCRIPTION OF THE DRAWINGS

To better understand what has been described above, several drawings schematically depicting a practical embodiment only by way of non-limiting example are attached.

In said drawings.

DESCRIPTION OF A PREFERRED EMBODIMENT

A preferred embodiment of the claimed device is described below in reference to FIGS. 1 to 9 mentioned above.

The preferred embodiment of the described device 1 for resuscitation has a nozzle 2 provided with an inlet 2a for insufflated air, an air conveying tube 3 provided with a curved portion 3c with an outlet 3a for said air to enter the throat of the victim, a first one-way valve 4 interposed between the air inlet 2a and the air outlet 3a and a second one-way valve 5 interposed between the nozzle 2 and said first valve 4. The two one-way valves 4, 5 allow the flow of air from the inlet 2a to the outlet 3a but prevent the flow of a fluid exhaled by the victim in the opposite direction.

The device 1 is characterized in that the upper end of the air conveying tube 3 has a straight portion 3b of the tube 3 which is configured for internally receiving the body of the first valve 4. The walls of this portion 3b of tube 3 include a pair of holes 6 communicating with apertures 4a of the body of the valve 4 to allow discharging the fluid exhaled by the victim to the outside.

In the described embodiment, the first one-way valve 4 has an obturating piston 7 which is associated with a spring 8 having the function of maintaining the piston 7 in an upper position in which said piston 7 keeps the passage of fluid towards the nozzle 2 closed by default. The insufflated air enters the mentioned valve 4 when the insufflated air pressure exceeds the reaction force of the spring 8 and the obturating piston 7 moves to a lower position along guides 9 provided inside the body of the same valve 4. In this lower position, the piston 7 is housed in a portion 4b of the body of the valve 4 that widens to allow the passage of air through the cavity leaving the piston 7 free. In this same lower position, side walls 7a of the piston 7 itself close the apertures 4a of the body of said one-way valve 4 to prevent the insufflated air from seeping out.

Figure 7:
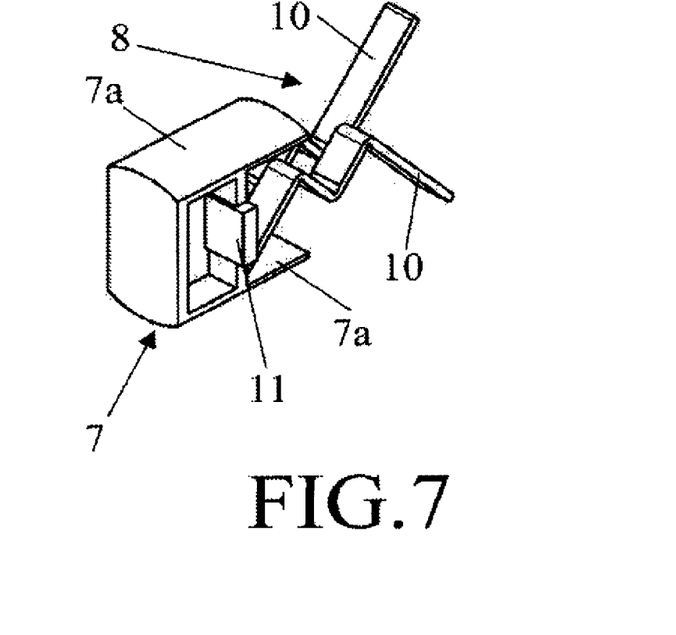
FIG. 7 is a perspective view showing the obturating piston of the first one-way valve in detail.

FIG. 7 shows a perspective view of the obturating piston 7 associated with the spring 8. As seen in FIG. 7, said spring 8 includes two zig-zag strips 10 which are attached to the side walls 7a of the piston 7. These walls 7a are particularly sized for closing the apertures 4a of the body of the valve 4 communicating with the outside. The same FIG. 7 also shows the projection 11 that moves between the guides 9 of the body of the valve 4 for guiding the piston 7 as it moves.

Figure 1:
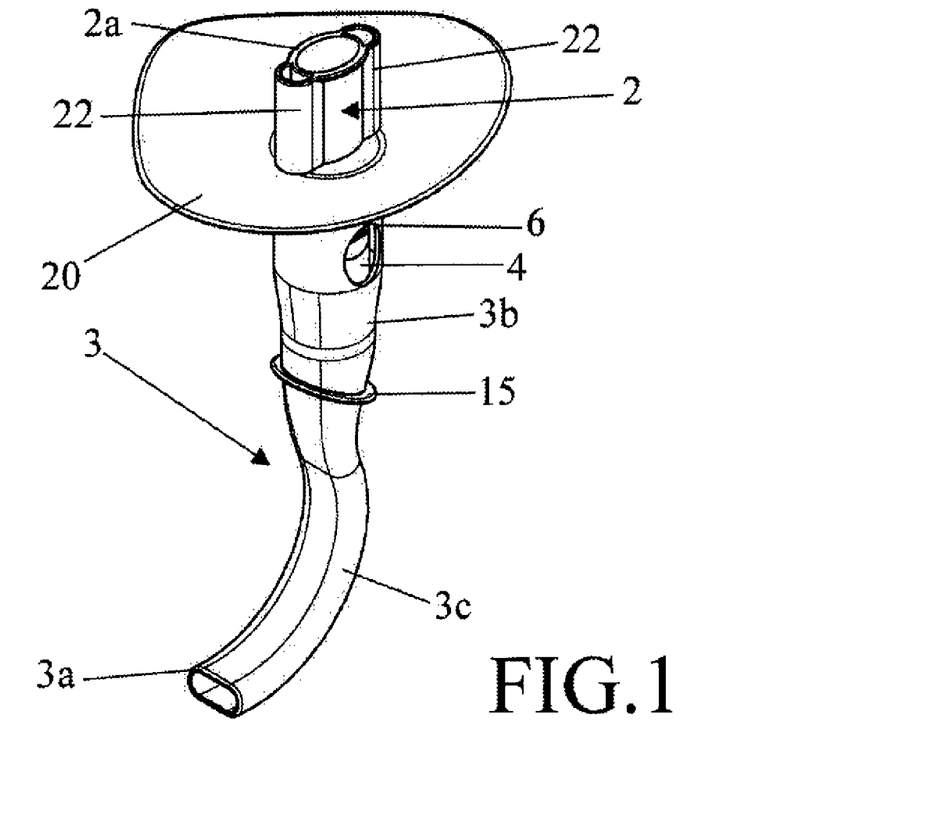
FIG. 1 is a perspective view of the device.
Figure 2:
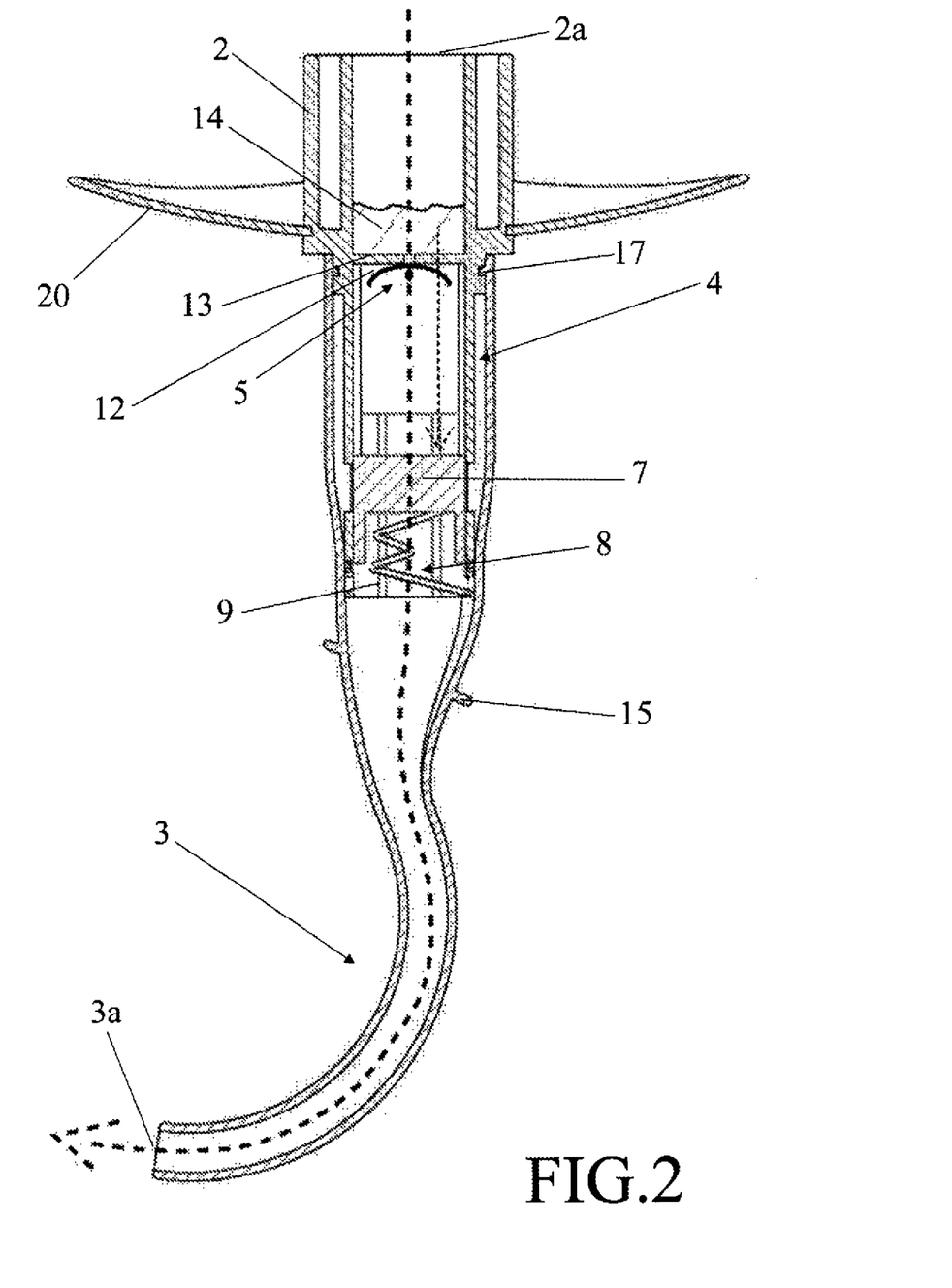
FIGS. 2 and 3 are two different longitudinal sections of the device of FIG. 1 showing the path taken by the flow of insufflated air from the air inlet to the outlet.
Figure 3:
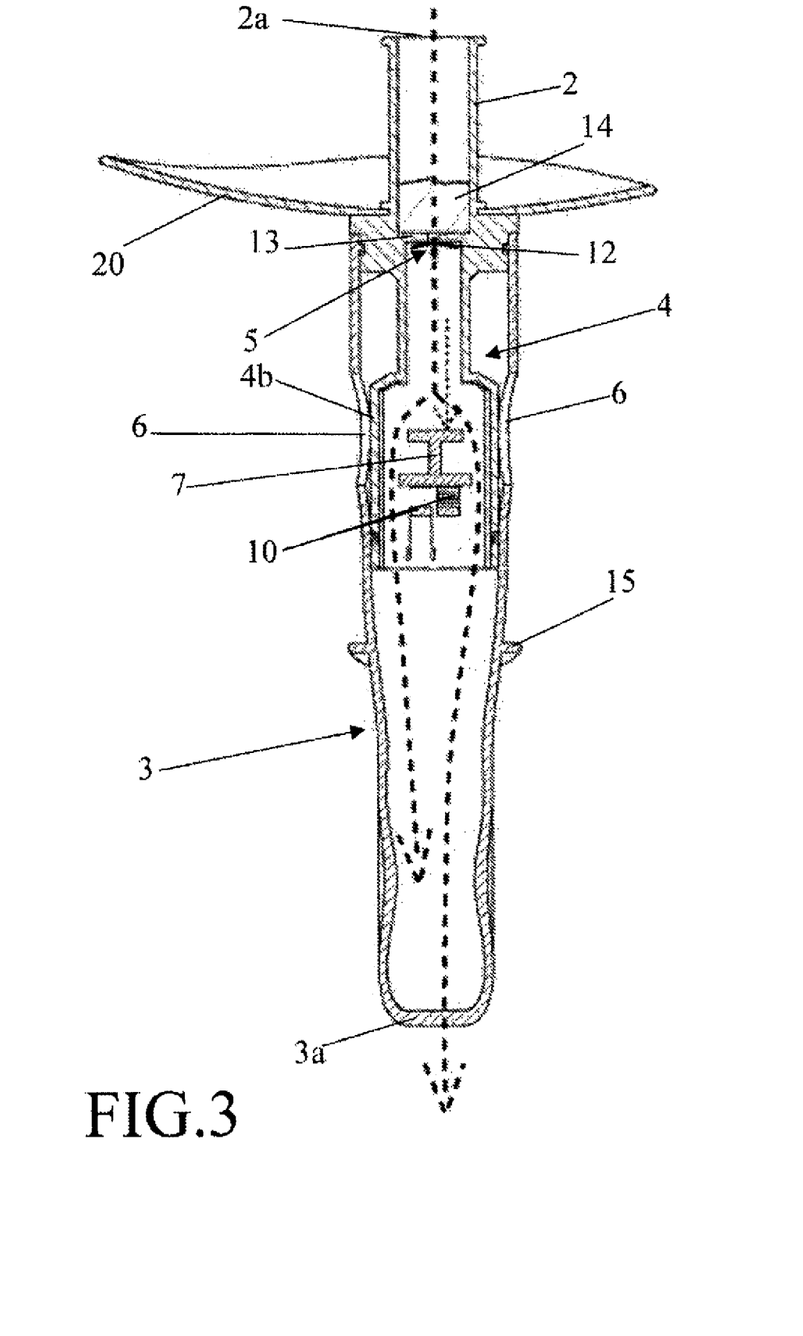

FIGS. 2 and 3 depict the path taken by the flow of insufflated air along the device 1. As can be seen, the insufflated air pressure acts on the piston 7 causing it to move to the lower position in which the walls 7a of said piston 7 close the outlet apertures 4a of the body of the valve 4. These same FIGS. 2 and 3 show the second one-way valve 5 of the device 1 which, in the described embodiment, is configured by a membrane 12 that can be bent by the incoming insufflated air pressure for opening the passage of air towards the first one-way valve 4. This flexible membrane 12 is anchored to the inner face of a seat 13 of the nozzle 2 which is provided with a layer of foam 14 which serves to retain moisture from saliva and microbes present in the insufflated air. Optionally, this layer of foam 14 can comprise a chemical compound for eliminating said microbes.

Figure 4:
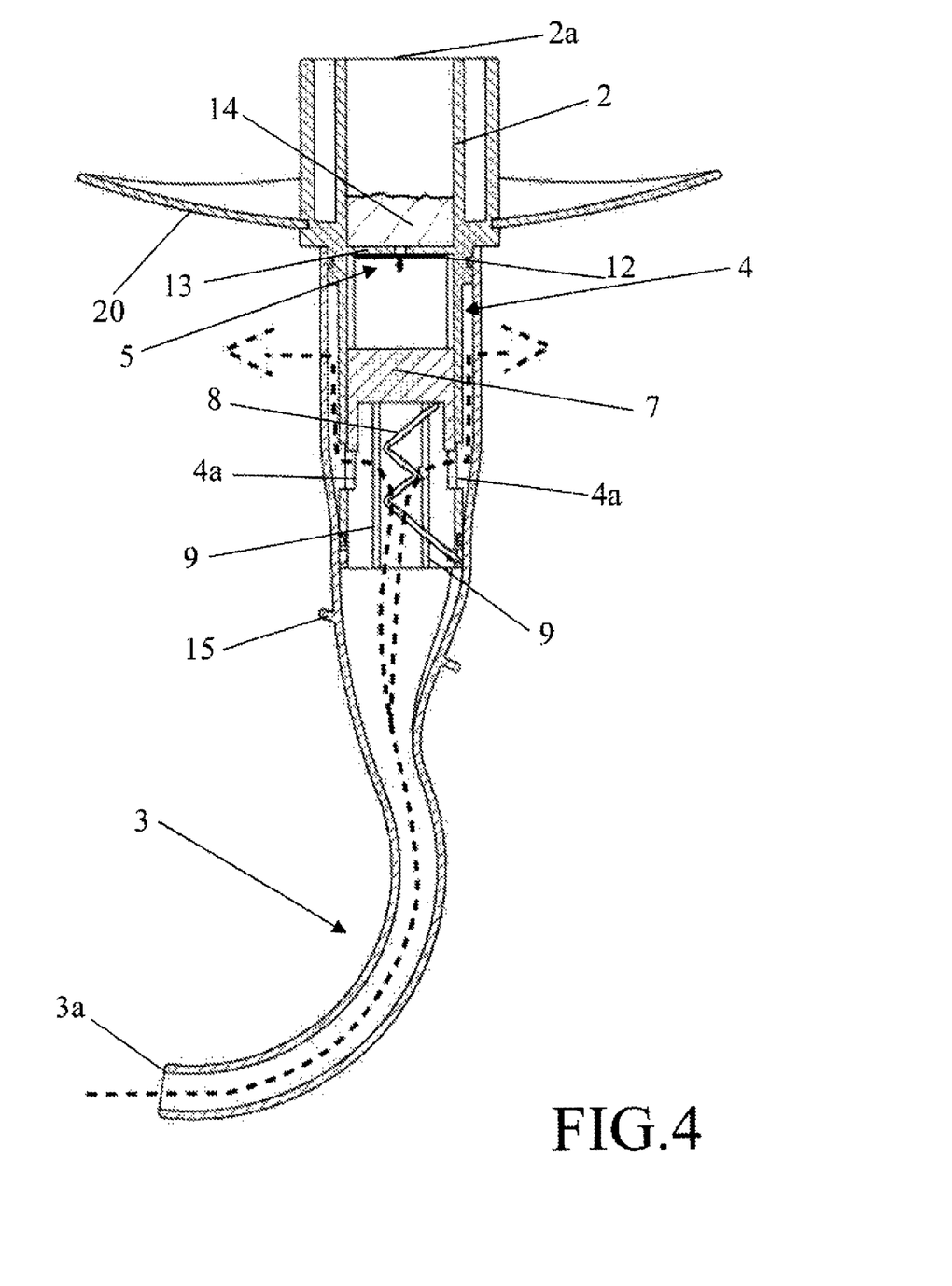
FIG. 4 is a longitudinal section of the device of FIG. 1 showing the path taken by a flow of fluid exhaled by the victim to reach the outer holes of the air conveying tube.

FIG. 4 depicts the path taken by a fluid exhaled by the victim. As can be seen in this FIG. 4, when the insufflated air pressure gives way, the piston 7 recovers the upper position as a result of the action of the spring 8. In this position, the outlet apertures 4a of the body of the valve are free from obstacles for allowing the exit of the exhaled fluid through the holes 6 of the air conveying tube 3.

In the described embodiment, the mentioned fluid discharge holes 6 are located in a position higher than the position of the apertures 4a of the body, therefore the fluid must run between the outer wall of the body of the valve 4 and the inner wall of the tube 3 itself in order to reach the discharge holes 6. Furthermore, in the described embodiment, the air conveying tube 3 has a translucent design to be able to detect the presence of exhaled fluid before it exits to the outside.

Figure 5:
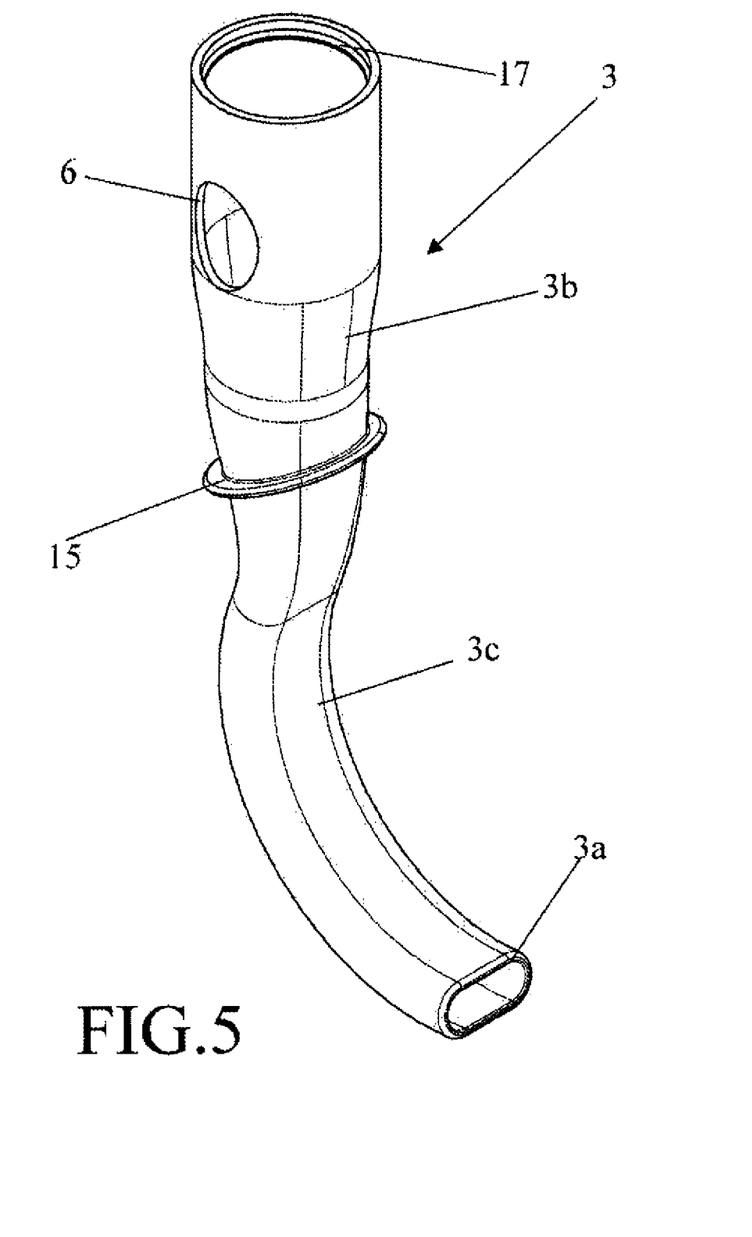
FIG. 5 is a perspective view of the air conveying tube lacking the valve and nozzle.

FIG. 5 shows a perspective view of the air conveying tube 3 without the valve 4 or the nozzle 2. This FIG. 5 shows an outer ring 15 abutting against the teeth and/or gums of the victim and separating the curved portion 3c of the tube from the portion 3b configured for receiving the body of the valve 4.

In the described embodiment, the outer ring 15 is fixed. Nevertheless, this very ring 15 can be detachable or can have a second ring, and can be provided, for example, with a projection to be able to be inserted in different positions of the outer wall of the tube depending on the size of the mouth and throat of the victim.

Figure 6:
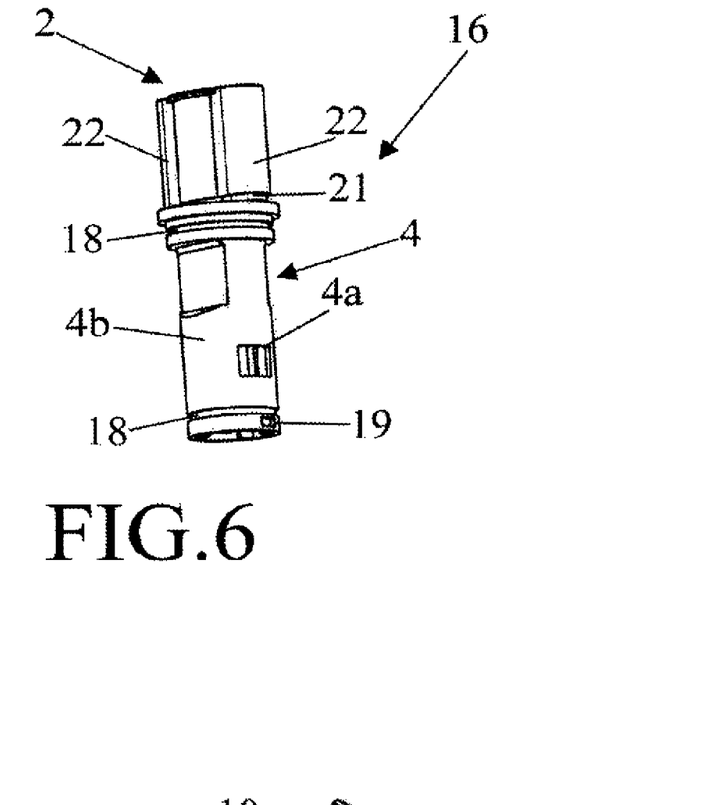
FIG. 6 is a perspective view showing the assembly of the nozzle and the body of the first one-way valve integrated in a single part.

FIG. 6 shows the assembly of the nozzle 2 and the body of the valve 4 integrated in a single part 16 that can be coupled to and uncoupled from the upper end of the air conveying tube 3. In the described embodiment, the coupling means for coupling the part 16 to the tube 3 are configured by projections 17 that can be inserted by pressure into annular grooves 18 provided in the outer walls of the part 16. Such coupling has the advantage of allowing the rotation of the part 16 in both directions about the axis of the tube 3 to be able to comfortably orient the nozzle 2. The same FIG. 6 also shows the holes 19 of the part 16 where the ends of the steel strips 10 of the spring 8 abutting against the walls of the tube 3 are inserted when the part 16 is arranged inside the portion 3b of the air conveying tube.

As mentioned in the description of the invention, the nozzle 2 is associated with a protective mask 20 for protecting the lips and nose and part of the face of the resuscitator which is provided with a hole the edges of which are snap-fitted into a notch 21 of the same nozzle 2. The nozzle 2 also includes side protuberances or reinforcements 22 which make holding same with the teeth in the mouth of the resuscitator easier.

Figure 8:
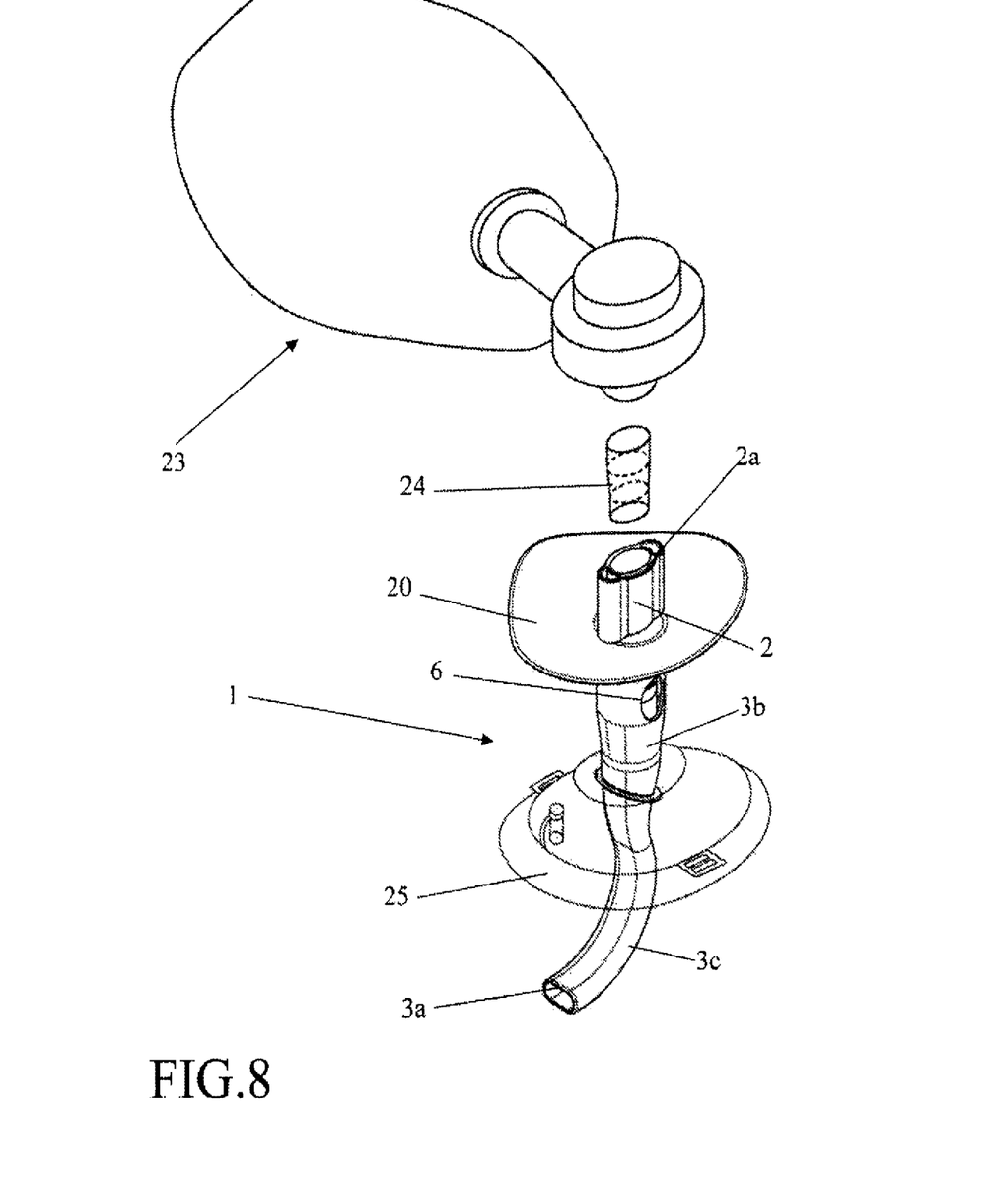
FIG. 8 is an exploded perspective view of the device showing a self-expandable resuscitation bag for insufflating air and an accessory for connecting the nozzle of the device to the mentioned bag.

FIG. 8 depicts an exploded perspective view of the device 1 ready to be used with a self-expandable resuscitation bag or balloon 23 for insufflating air (for example, an AMBU brand bag). In this case, the device 1 includes a connection reducing accessory 24 for connecting the inlet 2a of the nozzle 2 to the inlet of the bag 23.

The same FIG. 8 shows the mask 25 which serves to cover the mouth and nose of the victim. This mask 25 is also provided with a hole the edges of which are snap-fitted into the air conveying tube 3. Optionally, this very mask 25 can have an oxygen supply line.

To carry out the resuscitation procedure (see FIG. 9), the resuscitator must first insert the curved portion 3c of the tube 3 through the mouth to the pharynx of the victim. To that end, the resuscitator holds the device 1 in his/her hand using the straight portion 3b like a lever and, holding the mask that goes on the face of the victim, the tube 3 is introduced into the palate and then rotated 180°. The nozzle 2 associated with the mask 20 is oriented, if necessary, to assure the procedure. In this position, the device 1 is placed firmly over the mouth of the victim, so the resuscitator can also perform cardiac massages without the risk of moving the device 1.

Figure 9:
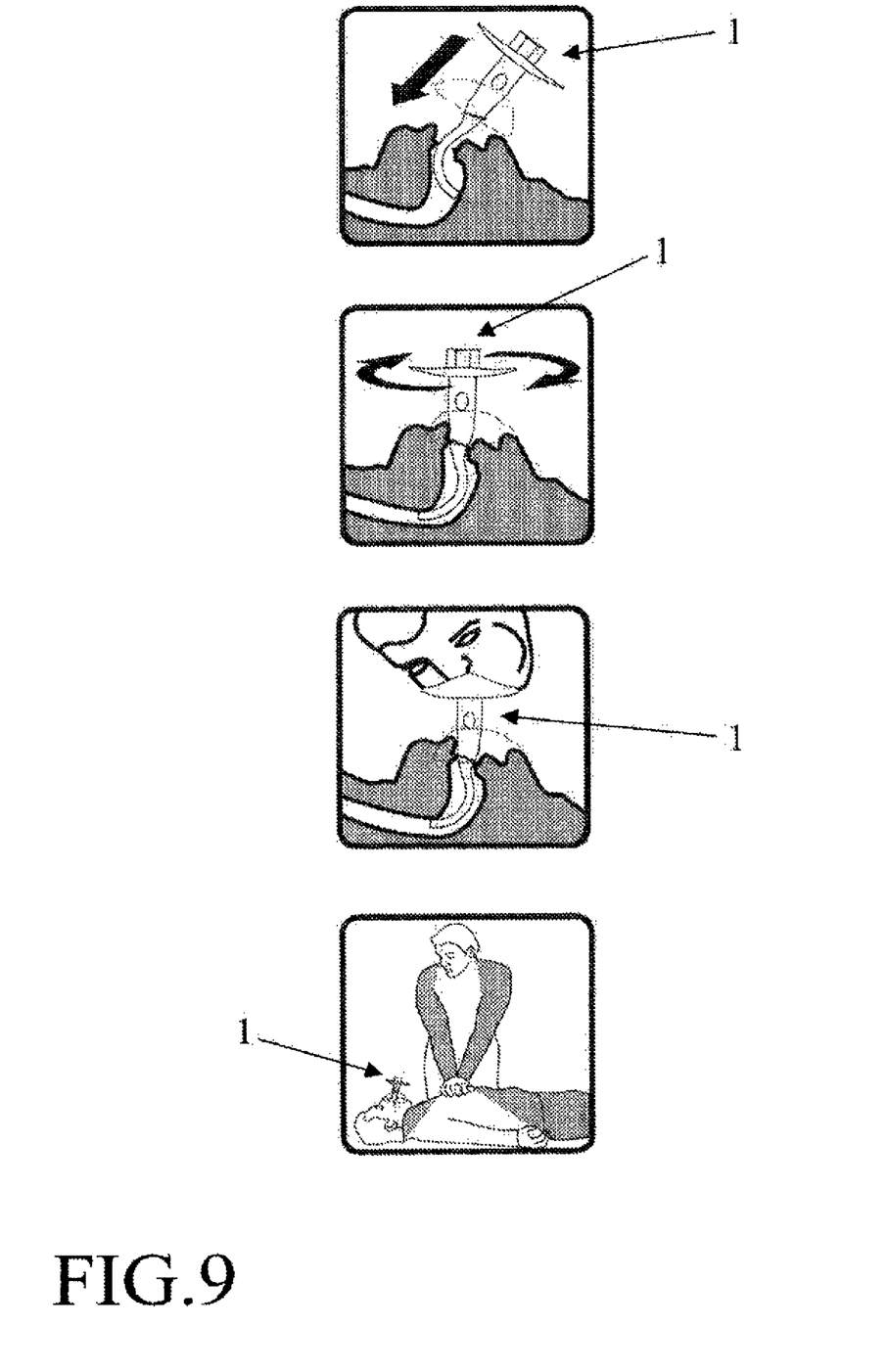
FIG. 9 depicts the steps of a resuscitation procedure with the device.

To introduce air, the resuscitator directly contacts the nozzle 2 or connects the resuscitation bag 23. While air is insufflated, the resuscitator is protected with the protective mask 20. When the victim exhales any type of fluid (air, blood or vomit), this fluid is expelled through the holes 6 of the air conveying tube 3. The curved portion 3c of the tube prevents any type of choking and assures correct air and fluid circulation to be able to resuscitate the victim quickly.

Despite having made reference to a specific embodiment of the invention, it is obvious for a person skilled in the art that the described device 1 is susceptible to various variations and modifications and that all the mentioned details can be replaced with other technically equivalent details without departing from the scope of protection defined by the attached claims.

The invention claimed is:

1. A device for resuscitating a patient or a victim of cardiorespiratory arrest comprising:
    an insufflated air inlet,
    an outlet for said insufflated air provided at a lower end of an air conveying tube designed to penetrate a throat of the patient or the victim through a mouth, wherein said insufflated air inlet is provided in a nozzle for contact with a mouth of a resuscitator, said nozzle including coupling means for coupling to the upper end of said air conveying tube;
    at least a first one-way valve interposed between said air inlet and air outlet to allow a flow of air from said inlet to said outlet and prevent a flow of a fluid exhaled by the patient or the victim in an opposite direction, a body of said valve including an outlet aperture for an exit of the fluid exhaled by the patient or the victim, characterized in that an upper end of said insufflated air conveying tube comprises a portion of tube which is configured for internally receiving the body of said valve, a wall of said tube including at least one outer hole communicating with an aperture of the body of the valve to allow discharging the fluid exhaled by the patient or the victim to an outside,
    wherein the body of said valve and said nozzle are integrated in a single part, said part being able to be coupled to and uncoupled from the upper end of said air conveying tube,
    wherein said first one-way valve comprises an obturating piston which is associated with a spring, said obturating piston being able to move inside the body of said valve to allow the entry of air when the insufflated air pressure exceeds the reaction force of the spring, the body of the valve comprising guides along which said piston moves, said piston closing the outlet aperture of the body of the valve as it moves along said guides due to the insufflated air pressure; and
    a protective mask for protecting lips and a nose and part of a face of the resuscitator which is configured for being coupled to the air inlet nozzle of the device, said mask being able to rotate together with said nozzle about the axis of the air conveying tube.

2. The device according to claim 1, wherein said coupling means are configured to allow the rotation of said nozzle in both a clockwise direction and a counterclockwise direction about an axis of said air conveying tube.

3. The device according to claim 1, wherein the lower end of said air conveying tube comprises a curved portion of the tube designed to penetrate a pharynx of the patient or the victim, said curved portion of the tube allowing holding down a tongue of the victim to prevent choking.

4. The device according to claim 1, wherein the wall of said air conveying tube comprises a ring abutting against the teeth and/or gums of the patient or the victim.

5. The device according to claim 1, wherein said air conveying tube is made of one of a translucent plastic material and a soft plastic material.

6. The device according to claim 1 comprising a second one-way safety valve which is interposed between said first one-way valve and a nozzle, said second one-way valve preventing the flow of a fluid exhaled by the victim in the opposite direction in the event that the first valve malfunctions.

7. The device according to claim 6, wherein said second one-way valve comprises a membrane for closing the passage of fluid towards the nozzle, said membrane being able to be bent by the insufflated air pressure for opening the passage of air towards the first one-way valve.

8. The device according to claim 1, wherein the body of said first valve comprises a pair of holes for inserting the ends of said spring, the wall of the air conveying tube abutting against said ends when the body of the first valve is housed therein.

9. The device according to claim 1 comprising a mask for covering the mouth and nose of the victim which is configured for being coupled to the upper end of said air conveying tube.

10. The device according to claim 1, wherein said nozzle comprises a seat provided with a layer of foam for retaining moisture and/or microbes present in the insufflated air.

11. The device according to claim 1 comprising an accessory for connecting the nozzle to a self-expandable resuscitation bag or balloon for insufflating air.

12. The device according to claim 1, wherein the outer hole of the insufflated air conveying tube is arranged at a height greater than a height of the outlet aperture of the first valve.

* * * * *